United States Patent [19]

Shapiro

[11] Patent Number: 5,439,464

[45] Date of Patent: Aug. 8, 1995

[54] METHOD AND INSTRUMENTS FOR PERFORMING ARTHROSCOPIC SPINAL SURGERY

[75] Inventor: David E. Shapiro, Highland Park, Ill.

[73] Assignee: Shapiro Partners Limited, Highland Park, Ill.

[21] Appl. No.: 28,244

[22] Filed: Mar. 9, 1993

[51] Int. Cl.$^6$ ............................................. A61B 17/00
[52] U.S. Cl. .................................... 606/83; 604/164; 604/264; 623/17; 606/79; 606/167
[58] Field of Search ................... 604/164, 264; 606/13, 606/79, 83, 90, 105, 167; 623/17, 18; 128/898

[56] References Cited

U.S. PATENT DOCUMENTS

| | | |
|---|---|---|
| 2,031,682 | 2/1936 | Wappler et al. |
| 2,068,721 | 1/1937 | Wappler et al. |
| 2,919,692 | 1/1960 | Ackermann . |
| 3,752,161 | 8/1973 | Bent . |
| 3,938,527 | 2/1976 | Rioux et al. |
| 3,996,921 | 12/1976 | Neuwirth ............................... 128/4 |
| 4,003,380 | 1/1977 | Wien . |
| 4,016,881 | 4/1977 | Rioux et al. |
| 4,418,692 | 12/1983 | Guay . |
| 4,461,281 | 7/1984 | Carson ................................ 128/898 |
| 4,539,976 | 9/1985 | Sharpe . |
| 4,545,374 | 10/1985 | Jacobson . |
| 4,573,448 | 3/1986 | Kambin ............................... 128/898 |
| 4,580,563 | 4/1986 | Gross . |
| 4,644,951 | 2/1987 | Bays . |
| 4,655,216 | 4/1987 | Tischer . |
| 4,662,371 | 5/1987 | Whipple et al. |
| 4,712,545 | 12/1987 | Honkanen . |
| 4,722,338 | 2/1988 | Wright et al. |
| 4,723,546 | 2/1988 | Zagorski . |

(List continued on next page.)

FOREIGN PATENT DOCUMENTS

| | | |
|---|---|---|
| 0515220A1 | 11/1992 | European Pat. Off. . |
| 903 | 7/1903 | France . |
| 2808911B1 | 3/1978 | Germany . |
| 2073026 | 4/1981 | United Kingdom . |

| | | |
|---|---|---|
| PCT/US91/- 08435 | 5/1992 | WIPO . |
| 9208513 | 5/1992 | WIPO . |

OTHER PUBLICATIONS

Copy of Partial European Search Report and Communication for EP 94 30 1639.

Primary Examiner—Stephen C. Pellegrino
Assistant Examiner—Sonya C. Harris
Attorney, Agent, or Firm—Pravel, Hewitt, Kimball & Krieger

[57] ABSTRACT

A method and apparatus for performing an arthroscopic spinal laminectomy or similar surgical procedure includes a plurality of cannulas which are individually inserted, in a predetermined sequence, into predetermined areas of a patient's spinal column. The first inserted cannula has a tissue manipulating surface thereon which is used to create a working space adjacent a predetermined area of the patient's spinal column. A viewing device is inserted through this cannula and the fluid used in association therewith is used to maintain the working space. The second and third cannulas are larger in size and are working cannulas in that they provide passageways for instruments used in the surgical procedure. The second and third cannulas are utilized by the surgeon to sequentially remove a portion of the ligamentum flavum necessary to expose the desired area of the patient's spinal bone and, if necessary, to remove any portion of bone necessary to expose the nerve and disc area. The nerves are then moved and the sequestered portion of the disc is removed, all utilizing the cannulas as passageways to perform the surgical procedure. In addition to a cannula which has a tissue manipulating surface thereon, the invention includes a rongeur having a cross section shaped to pass through a cannula and with a suction connection therefor so that whatever body tissue and/or bone fragments are cut by the rongeur may be removed by suction through the passageways created by the cannula.

8 Claims, 3 Drawing Sheets

U.S. PATENT DOCUMENTS

| | | |
|---|---|---|
| 4,733,663 | 3/1988 | Farley . |
| 4,785,826 | 11/1988 | Ward . |
| 4,985,030 | 1/1991 | Melzer et al. . |
| 4,990,148 | 2/1991 | Worrick, III . |
| 4,994,024 | 2/1991 | Falk . |
| 5,019,081 | 5/1991 | Watanabe . |
| 5,061,238 | 10/1991 | Shuler . |
| 5,061,269 | 10/1991 | Muller . |
| 5,089,000 | 2/1992 | Agee et al. . |
| 5,092,872 | 3/1992 | Segalowitz . |
| 5,122,134 | 6/1992 | Borzone et al. . |
| 5,122,139 | 6/1992 | Sutter . |
| 5,133,719 | 7/1992 | Winston . |
| 5,147,357 | 9/1992 | Rose et al. . |
| 5,152,772 | 10/1992 | Sewell, Jr. . |
| 5,160,318 | 11/1992 | Shuler . |

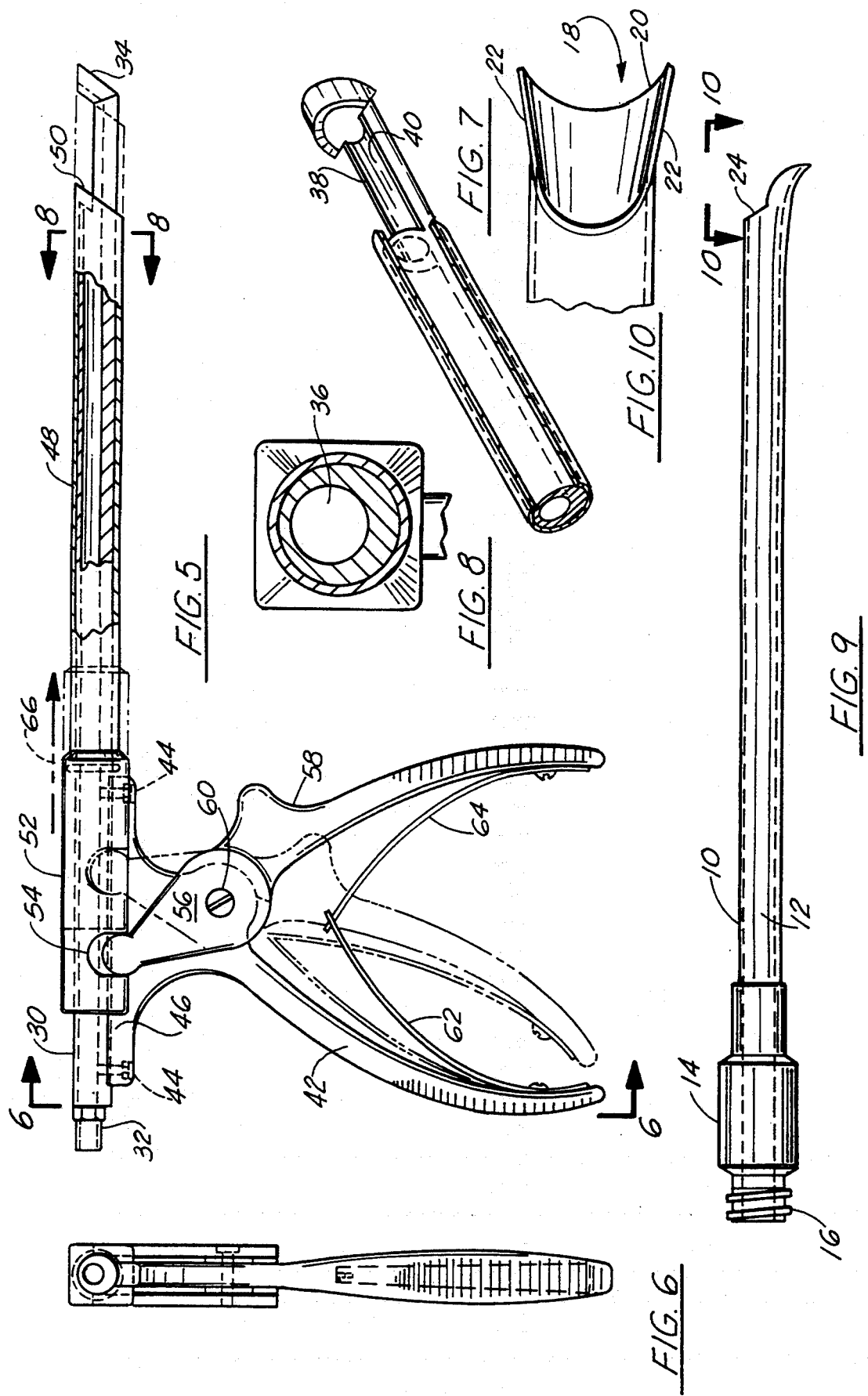

METHOD AND INSTRUMENTS FOR PERFORMING ARTHROSCOPIC SPINAL SURGERY

THE FIELD OF THE INVENTION

This invention relates to a method and instruments to perform an arthroscopic spinal procedure and, more specifically, a laminectomy, although the techniques and instruments disclosed are also useful in performing spinal fusions.

It is the present practice in performing laminectomies on the spine, whether in the cervical, thoracic, or lumbar regions, to follow a procedure in which there is some dissection of muscle and tissue by the surgeon. Although every attempt is made to minimize such dissection, the fact remains that it is necessary and it is a major factor in determining rehabilitation time for the patient which can range anywhere from six weeks to three months.

The present invention is specifically directed to applying the arthroscopic surgical techniques used on knees and shoulders to spinal surgery and, more specifically, to laminectomies. By utilizing arthroscopic techniques, muscle dissection is maintained at an absolute minimum and in many instances there may be no such dissection and the only invasion of the body will be the three small stab wounds necessary to insert the cannulas which provide the passageways for the procedure. The utilization of arthroscopic concepts in spinal surgery requires instruments not heretofore available. Specifically, a cannula is utilized which has a tissue manipulating or moving edge thereon which is used to create a space for subsequently used instruments. Also, since all of the surgical steps must be performed by utilizing cannulas as instrument passageways, it was necessary to develop new instrumentation which would pass through cannulas and yet still perform the necessary tissue and bone removal, nerve movement, and the final retraction of the herniated portion of the disc.

U.S. Pat. No. 4,545,374 describes a method and instruments for performing a percutaneous lumbar diskectomy. In this patent the lumbar region of the spinal column is accessed by laterally inserting a cannula through the patient's side. This technique has minimum utilization and will not permit the removal of approximately 80 percent of herniated discs in which the disc is sequestered and for that reason it has not been utilized to any substantial extent in performing spinal laminectomies.

SUMMARY OF THE INVENTION

The present invention relates to a method and instruments for arthroscopically accessing a predetermined area of a patient's spinal column and for subsequently performing desired surgical procedures thereon.

Another purpose of the invention is a method of arthroscopically performing a spinal laminectomy utilizing a plurality of cannulas, each of which provide instrument passages whereby the entire laminectomy may be performed with minimum body invasion and only requiring three small stab-type wounds for the insertion of the cannulas.

Another purpose of the invention is a method of performing a spinal laminectomy in which a plurality of cannulas are utilized and in which the initially inserted cannula has a tissue manipulating or moving surface thereon which is used to create a working space for the subsequently utilized instruments which will pass through the other cannulas.

Another purpose of the invention is to provide techniques for performing spinal laminectomies requiring the absolute minimum tissue and muscle dissection.

Another purpose of the invention is to provide a surgical technique for obtaining access to a predetermined area of the spinal column utilizing a plurality of cannulas as the instrument passages.

Another purpose of the invention is to provide a cannula for use in the surgical procedure described having a tissue moving or manipulating surface at one end thereof which is utilized to create a working space for subsequently applied instruments.

Another purpose of the invention is to provide rongeur cutting instruments having a cross sectional area of a size and shape to pass through cannulas for use in performing spinal surgical procedures utilizing arthroscopic techniques.

Another purpose of the invention is to provide a Kerison rongeur having suction capabilities for removing tissue and/or bone in the described surgical process.

Another purpose of the invention is to provide a surgical cutting instrument having a cross section shape and size adapted for use in surgical techniques in which the instrument must pass through a cannula and all subsequent manipulation thereof must be done through the cannula.

Other purposes will appear in the ensuing specification, drawings and claims.

BRIEF DESCRIPTION OF THE DRAWINGS

The invention is illustrated diagrammatically in the following drawings wherein:

FIG. 5 is a side view, in part section, illustrating a Kerison rongeur cutting instrument having a suction connection thereon, FIG. 6 is a view along plane 6—6 of FIG. 5;

FIG. 7 is an enlarged partial perspective illustrating a portion of the instrument of FIGS. 5 and 6;

FIG. 8 is an enlarged section along plane 8—8 of FIG. 5;

FIG. 9 is a side view of a cannula having a tissue manipulating surface thereon; and FIG. 10 is an enlarged partial top view of the tissue manipulating surface of the cannula of FIG. 9.

DESCRIPTION OF THE PREFERRED EMBODIMENT

Figure 1:
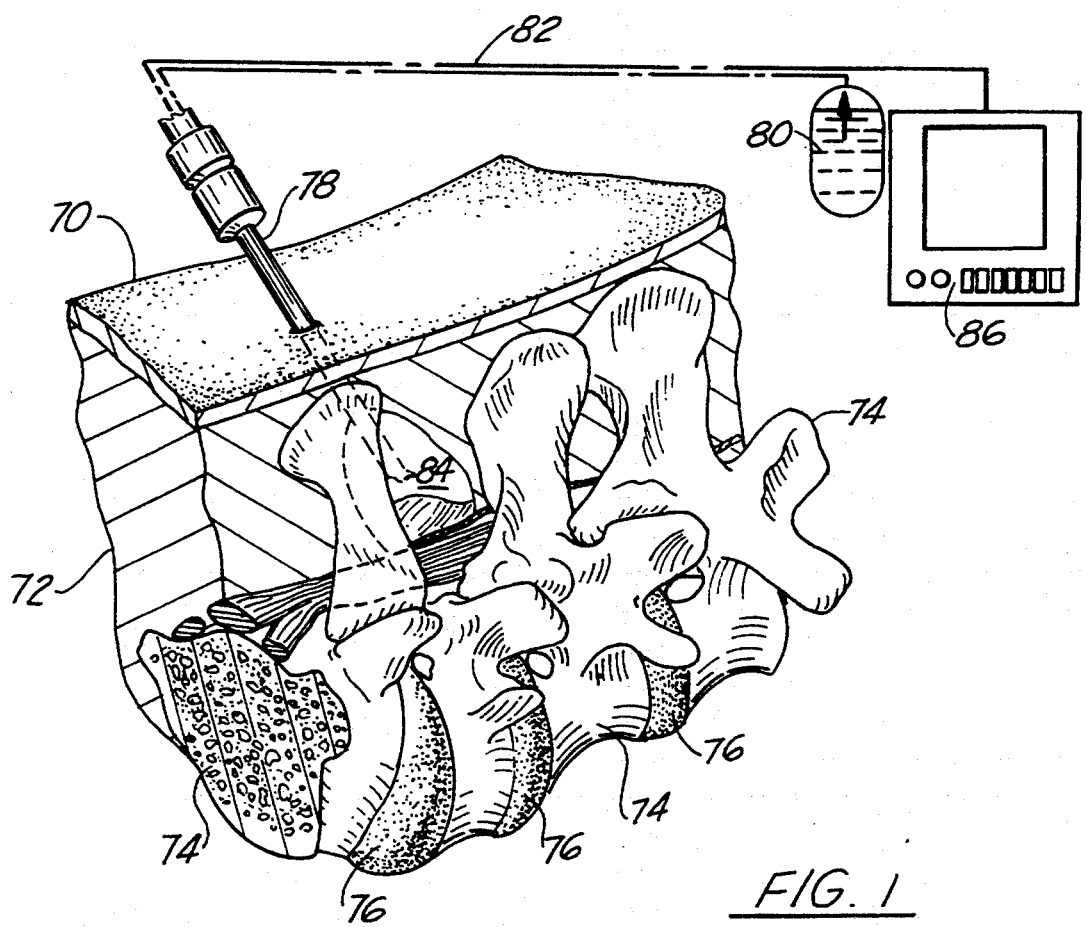
FIG. 1 is a diagrammatic illustration of a portion of the lumbar region of the spinal column illustrating the initial step in the described surgical procedure.

The invention will be described specifically in connection with a laminectomy in the lumbar region of the spine. It should be understood that the surgical technique described, as well as the disclosed instruments, may be used in performing spinal laminectomies utilizing arthroscopic techniques on the cervical and thoracic areas of the spine, as well as performing other surgical procedures, more specifically, spinal fusions.

In spinal laminectomies as this surgical procedure is currently performed, it is necessary to have some dissection of tissue and muscle to access the herniated disc. Even though every effort is made to minimize such dissection, it is necessary in order to obtain access to the disc and to insert the instruments necessary for removal of the sequestered portion of the disc. It is the dissection of the muscle and tissue and the associated trauma which determines the patient rehabilitation time. The less invasive the procedure, the quicker the patient will return to full activity. Rehabilitation time is meant to include not only time in the hospital, but the time before the patient can return to full time work or other activity.

It is present-day practice to perform arthroscopic surgical procedures on certain areas of the body, specifically the knee and shoulder, and these procedures, since they involve minimal invasion of the body, usually by puncture wounds, may be done on an outpatient basis, eliminating time spent in the hospital, and also substantially reducing the rehabilitation time before the patient returns to full time activity. The present invention is specifically directed to utilizing the concepts of arthroscopic surgery in performing spinal laminectomies and/or fusions. Before describing the surgical procedure, certain instruments which were not heretofore available will be described, which will lead to a fuller understanding of the surgical techniques.

In FIGS. 9 and 10 there is a cannula having a body 10 which is cylindrical in form and may be of a size utilized in arthroscopic knee and shoulder surgery. Body 10 has an internal cylindrical passageway 12 to accommodate a viewing scope and the fluid necessary for proper utilization of the scope. The body 10 may have an enlarged end 14 and a threaded end 16 for use in attaching the desired viewing instrumentation. Of specific importance in the cannula of FIGS. 9 and 10 is the interior end 18 which will be inserted into the patient's body in the desired location. There is a cutting edge 20 which may be termed a tissue manipulation or moving edge as it will perform more in the nature of tissue movement than it will tissue cutting or dissection. The edge 20 extends both radially and axially of the body 10. Looking particularly at FIG. 10 it should be noted that the arcuate edge 20 extends radially outwardly of opposite sides of the body 10 and has walls 22 which extend from the end 20 to the body and provide strength and integrity to the tip or cutting edge. As shown particularly in the side view of FIG. 9, the cutting edge 20 bends substantially radially beyond the circumference of the body with the exterior surface of the end flowing smoothly from the body to the cutting edge 20. There is a wall 24 which in part provides the opening connecting passageway 12 with the end of the cannula. By movement of the cannula once inserted, the surgeon can utilize the edge or surface 20 to manipulate the tissue and muscle as will be described subsequently herein.

FIGS. 5 through 8 disclose a Kerison rongeur suction punch. Kerison rongeur instruments are known in the art, as are suction instruments, which are commonly used in a number of surgical procedures. The instrument of FIGS. 5 through 8 combines a Kerison rongeur with a suction adapter so that particles removed by the cutting action of the instrument may be eliminated from the working area. Of particular importance is the fact that the cross sectional area of the Kerison rongeur is of a size and shape to pass through a cannula. In this connection, the invention encompasses other types of surgical cutting instruments which do not have suction connections therefor, but which have a cross sectional area of a size and shape so that they may pass through working cannulas to reach the area of interest for the surgeon.

In FIGS. 5 through 8 the instrument has a body 30 which has a suction connection 32 at one end thereof and a cutting tip 34 at the opposite end thereof. The body 30, which is cylindrical in a major portion of its length, has an axially extending passage 36 which connects to the suction attachment 32 and, as particularly shown in FIGS. 7 and 8, is radially offset from the axis of the body. Body 30 has a recess 38 adjacent the cutting end 34 to form a trough 40 which functions as a receptacle for severed tissue and/or bone prior to such particles being drawn through the suction passage 36. Body 32 is attached to a fixed handle element 42 by a pair of fastening elements 44 which connect the platform portion 46 of the fixed handle 42 to the underside of the body.

Coaxially mounted on body 30 is a movable sleeve 48 which has a cutting edge 50 at one end thereof which cooperates with the cutting edge 34 to sever pieces of tissue and/or bone upon coaxial movement of the sleeve 48 relative to the body. Sleeve 48, as particularly shown in FIGS. 7 and 8, has a round cross section throughout a major portion of its length so that it may be received within a cannula to perform certain surgical procedures while so positioned. Sleeve 48 has an enlarged portion 52, illustrated in FIG. 8, and which, as shown, may be generally square in cross section, but could be otherwise. The enlarged portion 52 is pivotally attached through a slot 54 to an arm 56 of a movable handle 58. Handle 58 and the fixed handle 42 are pivotally attached together, for example by a screw connection 60. A pair of cooperating and interconnected leaf springs 62 and 64 bias the handles 42 and 58 to the open position of FIG. 5. When the handles are squeezed together, against the action of leaf springs 62 and 64, sleeve 48 will slide to the right, in the direction of arrow 66, so that the cutting edges 50 and 34 are brought together. These edges are sharp and the bringing together of these edges, as in a typical Kerison rongeur type of cutting action, will sever whatever is positioned between them.

Of importance in the instrument of FIGS. 5 through 8 is the fact that the cross section of sleeve 48 and that portion of the instrument where the cutting action occurs is round or circular so that it will loosely fit within a working cannula. All functions of the instrument are performed while it is so positioned and it is thus necessary that the cross section of the major portion of the pistol grip Kerison rongeur suction punch described match the interior of the cannula. Suction attached to fitting 32 is effective to remove any particles which are severed by the described cutting action.

Figure 2:
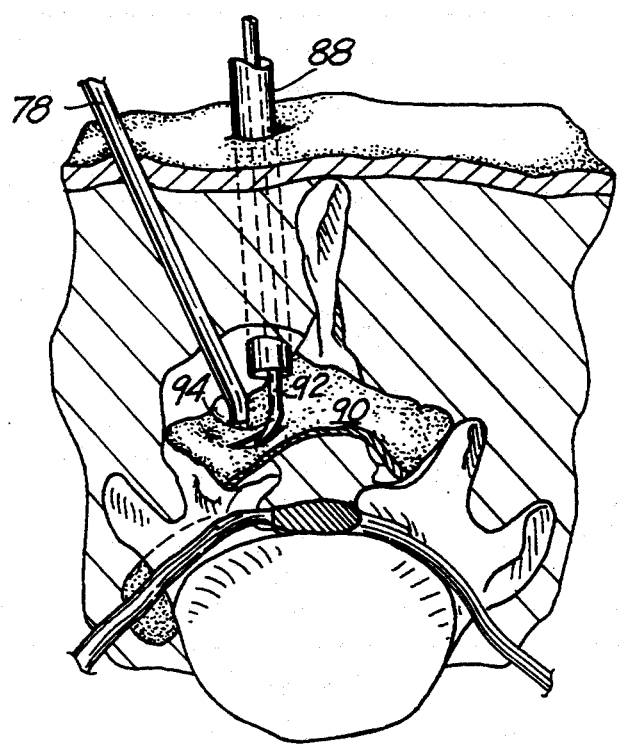
FIG. 2 is a partial transverse section through the spinal column illustrating the second step in the described surgical procedure.

The surgical procedure is illustrated on a step-by-step basis in FIGS. 1 through 4. As indicated earlier, the procedure will be described in connection with an arthroscopic spinal laminectomy, although the techniques described essentially provide arthroscopic access to an area of the spine and a fusion or other procedure may also be performed using the instruments and techniques described. In FIG. 1 the outer skin of the patient is indicated at 70 and muscle and other tissue is indicated at 72. The bone of the spinal column is indicated at 74 and spinal discs are indicated at 76. The initial step in the procedure is to insert a cannula 78 which is of the type illustrated in FIGS. 9 and 10 through the skin, tissue, and muscle into an area adjacent to and spaced laterally from the spinal column. More specifically, as shown in FIGS. 1 and 2, the cannula 78 is inserted through the outer skin 70 and muscle 72 in a generally posterolateral direction relative to the spinal column 74. A viewing scope will be passed through the cannula and fluid will be supplied from a source 80 along a line 82 so that fluid passes through the cannula 80 to an area 84 at the end of the inserted cannula. The surgeon may utilize a viewing screen 86 to have a full picture of the area in which the interior end of the cannula is working. The purpose of the cutting or tissue moving end of the cannula is so that the surgeon may manipulate it to create the working space 84. This is done by moving muscle and/or tissue rather than cutting it and the pressure of the fluid which is utilized in the viewing scope, which is of a type conventional in arthroscopic surgery, will maintain the space once it has been created. The pressure of the fluid within space 84 will keep or maintain the muscle and tissue away from the area in which the surgeon wishes to work.

Figure 3:
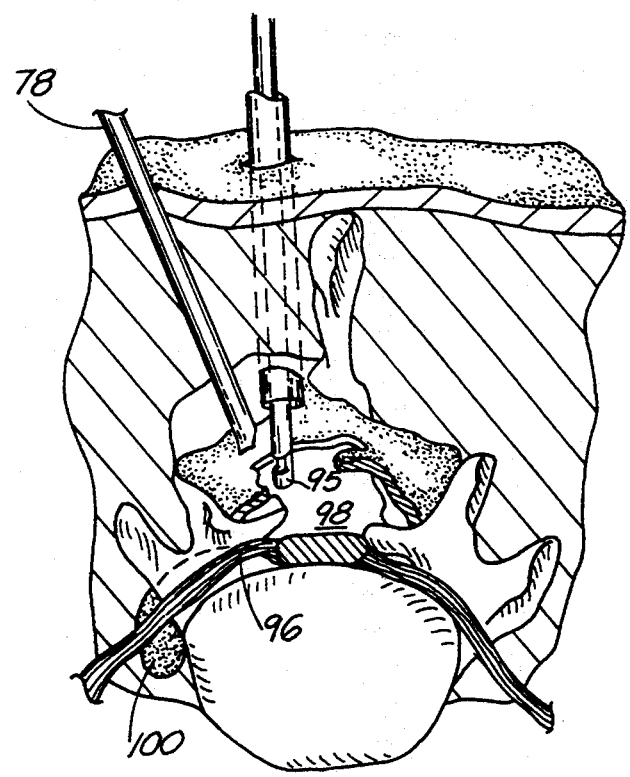
FIG. 3 is a transverse section, similar to FIG. 2, illustrating a further step in the described surgical procedure.
Figure 4:
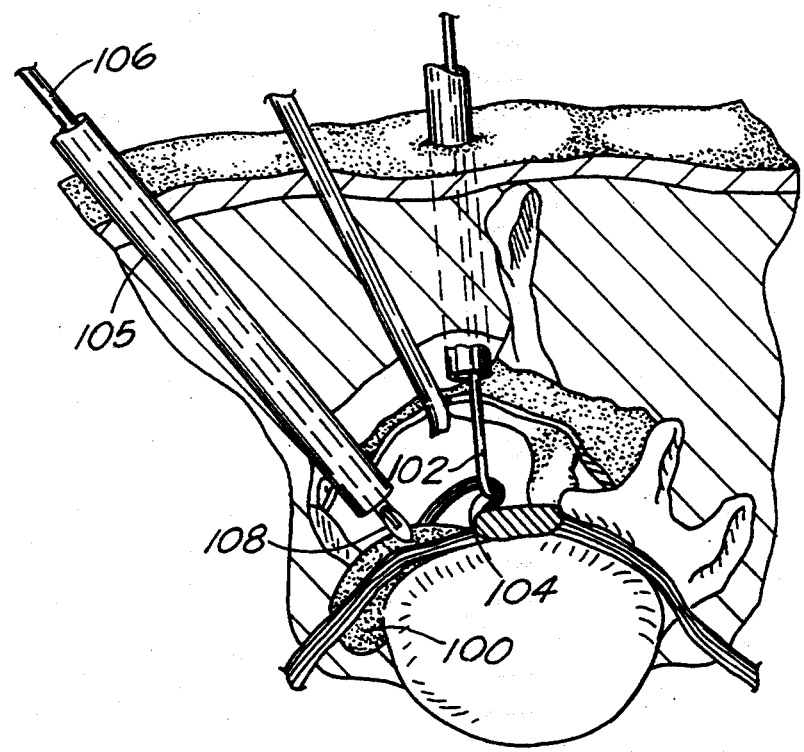
FIG. 4 is a transverse section, similar to FIGS. 2 and 3, illustrating yet a further step in the described surgical procedure.

Once the space 84 has been created as described, a second cannula 88, having an internal diameter slightly greater than the cannula 78, is inserted generally between the cannula 78 and the midline of the spinal column 74 as illustrated particularly in FIG. 2. The space 84 which was created as described above exposes the ligamentum flavum illustrated at 90 in FIG. 2 and the next step in the procedure is for the surgeon to insert a cutting tool, such as that illustrated at 92, having a cutting end 94 through working cannula 88. Ligamentum flavum is an elastic tissue which spans the space between adjacent vertebrae as particularly illustrated in FIG. 2. The cutting element or curette 92 will incise the ligamentum flavum, for example by making a slit at the superior edge of the inferior lamina. Once this slit has been made, the Kerison rongeur suction punch 95 illustrated in FIGS. 5–8 will be inserted through cannula 88, as illustrated in FIG. 3, to remove sufficient portions of the ligamentum flavum to expose the bone beneath it. In some instances it may be necessary to use the Kerison rongeur suction punch to actually remove portions of bone, as what is required is that the ligamentum flavum and/or bone be removed to a sufficient extent to expose the spinal nerves indicated generally at 96. Note particularly the opening 98 in the ligamentum flavum in FIG. 3.

At this point in the procedure the disc is accessible to the surgeon and the herniated portion of the disc indicated at 100 can be removed. The first step in removing the sequestered fragment 100 of the disc is to move nerves 96. This is done by inserting an instrument 102, illustrated in FIG. 4, through cannula 88 and gently slipping the hooked end 104 beneath the nerves and moving the nerves a sufficient distance to provide complete access to the sequestered portion 100 of the disc. Once the nerves have been so moved, a third cannula 105 is utilized. This cannula may be inserted at any point in the procedure once the nerves and bone have been exposed by removal of the necessary portion of the ligamentum flavum. Cannula 105, again a working cannula and of essentially the same internal diameter as cannula 88, will provide an access passage for a grabbing or clamping instrument 106 which has an operating end 108 of the type to grasp the sequestered portion 100 of the herniated disc and remove it. The herniated portion of the disc is then withdrawn through cannula 105. The relative positions of the three cannulas will vary depending upon the exact location of the damaged area of the spinal column. The positions shown in FIGS. 1–4 are merely illustrative.

Approximately 80 percent of herniated discs are sequestered which means that the herniated portion has actually broken away from the body of the disc. Even in those instances in which the herniated portion is not sequestered, it still may be removed as described. In some instances it may be necessary, prior to removing the herniated portion of the disc, to use a knife again inserted through the third cannula 105, to excise any tissue which may be overlying the disc. The important point, however, is that all of the described steps in the surgical procedure are performed arthroscopically through the described cannula passages and the various tools which may be necessary to first expose the nerves, then move the nerves, and then grasp the herniated portion of the disc, will all be utilized in the cannula passages described.

Once the steps described above have been completed and the herniated portion of the disc has been removed, all that remains is for the surgeon to withdraw the cannulas and suture the puncture wounds which were the only invasions of the body necessary for the entire surgical procedure.

Of importance in the procedure described is the minimal movement of body tissue and muscle and the lack of any incising or cutting of body tissue and muscle. This substantially reduces rehabilitation time and will permit the operation to be performed on an outpatient basis.

Although the procedure has been described in connection with a laminectomy, it should be clear to one skilled in the art that once the area of the bone is exposed as described, bone particles and/or bone segments for a fusion may also be inserted through a cannula and properly positioned for that type of procedure. Again, the procedure is not limited to access of the lumbar region of the spine, but may be equally utilized in the cervical or thoracic areas of the spine.

Whereas the preferred form of the invention has been shown and described herein, it should be realized that there may be many modifications, substitutions and alterations thereto.

What is claimed is:

1. A method for arthroscopically accessing a predetermined area of a patient's spinal column including the steps of inserting a first cannula into a patient's back in an area that is in a generally posterolateral position relative to a patient's spine, said first cannula having a first and second end with said first end passing through tissue and having an outwardly directed tissue moving surface;

inserting fluid utilizing viewing means through said first cannula, moving muscle and/or tissue through manipulation of the tissue moving surface of the first cannula to create a working space, said fluid of the viewing means being under pressure with said fluid pressure maintaining the working space created by the manipulation of the first cannula;

inserting a second cannula into the patient's back in a predetermined position relative to the first cannula;

inserting a cutting instrument through the second cannula and into the working space to incise the ligamentum flavum adjacent the working space to expose bone in the area that is generally in a posterolateral position relative to the patient's spine; and inserting a third cannula into the patient's back in a predetermined position relative to the first and second cannulas, and thereafter conducting an arthroscopic spinal surgical procedure on the spinal column by manipulating instruments through said second and third cannulas.

2. The method of claim 1, wherein said tissue moving surface of the first cannula extends in a radial direction from the first end of said cannula.

3. The method of claim 1, wherein the first cannula is inserted into the patient's back in an area of a lumbar region of the spinal column.

4. The method of claim 1, wherein the arthroscopic spinal surgical procedure performed through the use of the inserted cannulas includes a laminectomy.

5. A method of performing an arthroscopic laminectomy in a predetermined area of a patient's spinal column including the steps of:

inserting a first cannula having a body, a first end and a second end into a patient's back in an area that is in a generally posterolateral position relative to a patient's spinal column, said first end of the cannula having a tissue manipulating surface;

inserting fluid utilizing viewing means through said first cannula;

moving muscle and tissue through manipulation of the first cannula and its tissue manipulating surface to create a working space adjacent the patient's spinal column, said fluid of the viewing means being under pressure with said fluid pressure maintaining the working space;

inserting a second cannula into the patient's back in a predetermined position relative to the first cannula;

inserting a cutting instrument through the second cannula and into the working space to incise the ligamentum flavum adjacent the working space;

inserting a cutting/suction instrument through the second cannula and into the working space to remove a portion of the ligamentum flavum sufficient to expose a nerve and disc area of the spinal column;

inserting a nerve moving instrument through the second cannula and into the working space to move sufficient nerves to expose the spinal column disc area;

inserting a third cannula into the patient's back in a predetermined position relative to the first and second cannulas; and inserting a grasping instrument through the third cannula to grasp and remove a herniated portion of the spinal disc.

6. The method of claim 5, wherein the tissue manipulating surface on the first cannula extends in a radial outward direction from the first end of the first cannula.

7. The method of claim 6, wherein the first cannula tissue manipulating surface has a sharp curved end that is wider than the body of the cannula and said sharp end extends in a radial outward direction from the body of the cannula.

8. The method of claim 5, wherein the cutting/suction instrument inserted through the second cannula includes a rongeur cutting means.

* * * * *